(12) United States Patent
Wan et al.

(10) Patent No.: US 9,200,086 B2
(45) Date of Patent: Dec. 1, 2015

(54) NANOSILVER COATED BACTERIAL CELLULOSE

(71) Applicant: AXCELON BIOPOLYMERS CORPORATION, London (CA)

(72) Inventors: Wankei Wan, London (CA); Ganesh Guhados, Burnaby (CA)

(73) Assignee: AXCELON BIOPOLYMERS CORPORATION, London, ON (CA)

( * ) Notice: Subject to any disclaimer, the term of this patent is extended or adjusted under 35 U.S.C. 154(b) by 0 days.

(21) Appl. No.: 13/758,582

(22) Filed: Feb. 4, 2013

(65) Prior Publication Data

US 2013/0211308 A1 Aug. 15, 2013

Related U.S. Application Data

(63) Continuation of application No. 12/226,669, filed as application No. PCT/CA2007/000682 on Apr. 24, 2007, now Pat. No. 8,367,089.

(60) Provisional application No. 60/794,136, filed on Apr. 24, 2006.

(51) Int. Cl.
| | |
|---|---|
| *A01N 25/08* | (2006.01) |
| *A61K 9/70* | (2006.01) |
| *A01N 59/16* | (2006.01) |
| *C08B 15/05* | (2006.01) |
| *A61L 15/46* | (2006.01) |
| *C08B 15/02* | (2006.01) |
| *D06M 11/83* | (2006.01) |
| *D06M 23/08* | (2006.01) |
| *D06M 16/00* | (2006.01) |
| *A61L 15/28* | (2006.01) |
| *B82Y 5/00* | (2011.01) |

(52) U.S. Cl.
CPC ............... *C08B 15/05* (2013.01); *A61L 15/28* (2013.01); *A61L 15/46* (2013.01); *C08B 15/02* (2013.01); *D06M 11/83* (2013.01); *D06M 16/00* (2013.01); *D06M 23/08* (2013.01); *A61L 2300/104* (2013.01); *A61L 2300/404* (2013.01); *A61L 2300/606* (2013.01); *A61L 2300/624* (2013.01); *B82Y 5/00* (2013.01); *Y10S 977/762* (2013.01); *Y10S 977/773* (2013.01); *Y10S 977/788* (2013.01); *Y10S 977/81* (2013.01); *Y10S 977/904* (2013.01); *Y10T 428/249921* (2015.04); *Y10T 428/2927* (2015.01); *Y10T 428/2958* (2015.01); *Y10T 442/699* (2015.04)

(58) Field of Classification Search
CPC .......................................................... B82Y 5/00
See application file for complete search history.

(56) References Cited

U.S. PATENT DOCUMENTS

| | | | | |
|---|---|---|---|---|
| 3,930,000 | A * | 12/1975 | Margraf .................... | 514/184 |
| 6,333,093 | B1 * | 12/2001 | Burrell et al. ............ | 428/194 |
| 6,800,753 | B2 * | 10/2004 | Kumar ...................... | 536/57 |
| 7,390,760 | B1 * | 6/2008 | Chen et al. ................ | 442/341 |
| 2004/0241436 | A1 * | 12/2004 | Hsieh et al. .............. | 428/361 |

(Continued)

*Primary Examiner* — Scott Long
*Assistant Examiner* — Sarah Alawadi
(74) *Attorney, Agent, or Firm* — Lynn C. Schumacher; Stephen W. Leonard; Hill & Schumacher

(57) ABSTRACT

Nanosilver coated bacterial cellulose nanofiber and a method of producing the nanosilver coated bacterial cellulose nanofiber. The nanosilver coated bacterial cellulose nanofiber is produced by preparing a suspension of bacterial cellulose fibers, oxidizing bacterial cellulose fibers; adding the thio-group to the polymer backbone; reacting the resulting product with silver proteinate and enhancing the nanosilver particle size. The nanosilver coated bacterial cellulose nanofibers exhibit antimicrobial properties.

23 Claims, 5 Drawing Sheets

(56) References Cited

U.S. PATENT DOCUMENTS

| | | | |
|---|---|---|---|
| 2007/0003603 A1* | 1/2007 | Karandikar et al. | 424/443 |
| 2007/0053960 A1* | 3/2007 | Brown et al. | 424/445 |
| 2007/0100269 A1* | 5/2007 | Addison et al. | 602/48 |
| 2007/0237810 A1* | 10/2007 | Wellinghoff | 424/445 |

* cited by examiner

E. coli after 3 days
BC - control

E. coli after 3 days
1 hr oxidized (BC-SP)

E. coli after 3 days
1 hr – oxidized (BC-Ag)

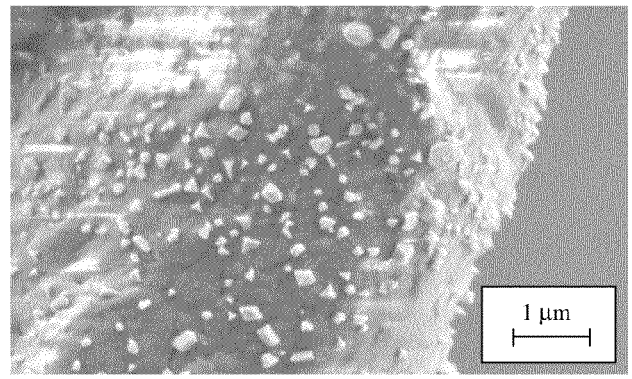
Figure 5
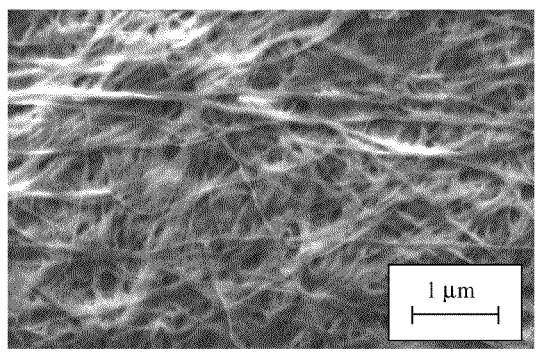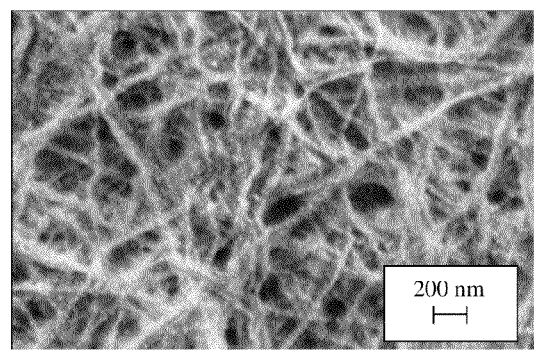
Figure 6A                              Figure 6B

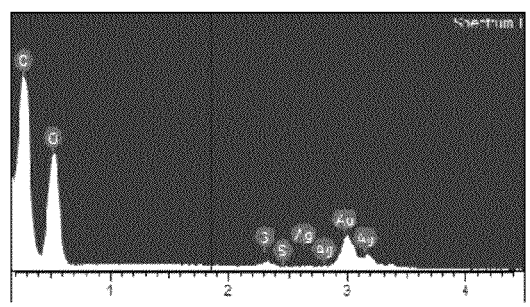
Figure 7
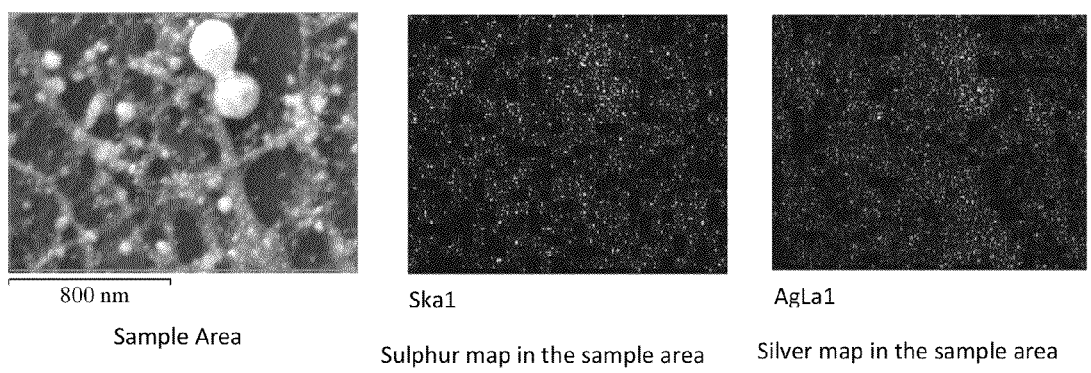
| Sample Area | Sulphur map in the sample area | Silver map in the sample area |
|---|---|---|
| Figure 8A | Figure 8B | Figure 8C |

# NANOSILVER COATED BACTERIAL CELLULOSE

CROSS REFERENCE TO RELATED U.S. APPLICATIONS

This patent application is a continuation of U.S. patent application Ser. No. 12/226,669, which relates to, and claims the priority benefit from, U.S. Provisional Patent Application Ser. No. 60/794,136 filed on Apr. 24, 2006, in English, entitled NANOSILVER COATED BACTERIAL CELLULOSE, and which is incorporated herein by reference in its entirety.

FIELD OF INVENTION

The present invention relates to an antimicrobial material comprising a cellulose incorporated with silver nanoparticles, chemically bound to the cellulose matrix, a process of making such material and its conversion into forms suitable for specific applications.

BACKGROUND OF INVENTION

Antimicrobial activity of colloidal silver is well known since the $19^{th}$ century. Silver is generally a safe and effective antimicrobial metal. Silver has been studied for antibacterial purposes in the form of powder, metal-substituted zeolite, metal-plated non-woven fabric, and crosslinked compound. The two main forms of silver are ionic form ($Ag^+$) and the metallic form($Ag^0$) and their mechanism of action is still under debate. Antibacterial cloth containing metallic particles (particularly copper, silver, and zinc in the form of zeolite) is known in the field for a long time. Many methods for incorporating the metal ions directly into a substrate material have been proposed. However, in the methods in which the metals are used directly, the incorporation of metals leads to very expensive products, with heavy weights as they are necessarily used in large amounts.

There are also methods that use polymeric substance to hold the metallic ions. For example, the method of binding or adding fine wires or powder of the metals themselves to a polymer and the method of incorporating compounds of the metals into a polymer. However, the products obtained by these methods show poor durability of antibacterial performance and can be utilized only for restricted purposes because the metal ions are merely contained in or attached to the polymer and, accordingly, they easily fall away from the polymer while being used.

Japanese Patent No. 3-136649 discloses an antibacterial cloth that has been prepared using $AgNO_3$. The $Ag^+$ ions in $AgNO_3$ are crosslinked with polyacrylonitrile. Such an antibacterial cloth demonstrates anti-bacterial activity against six bacterial strains including *Streptococcus* and *Staphylococcus*.

Japanese Patent No. 54-151669 discloses a fiber treated with a solution containing a compound of copper and silver. The solution is evenly distributed on the fiber, which is used as an anti-bacterial lining inside boots, shoes, and pants.

U.S. Pat. No. 4,525,410 discloses the use of closely packed with synthetic fibres and a specific zeolite particle that possess antimicrobial activity. In yet another approach, U.S. Pat. Nos. 5,496,860 and 5,561,167 disclose an antibacterial fiber produced through an ion exchange reaction. The antibacterial fiber includes an ion exchange fiber and an antibacterial metal ion entrapped within the ion exchange fiber.

U.S. Pat. No. 5,985,301 discloses a production process of cellulose fiber characterized in that tertiary amine N-oxide is used as a solvent for pulp, and a silver-based antibacterial agent and optionally magnetized mineral ore powder are added, followed by solvent-spinning.

U.S. Pat. No. 6,979,491 describes a method to produce nanosilver based antimicrobial yarn. Silver nitrate solution is reduced using a solution of glucose to produce 1-100 nanometers of silver particles. This solution is then soaked in the solution of nanoparticles.

U.S. Pat. No. 5,454,886 discloses the method of producing nanometallic silver to coat medical devices. The use of physical vapour deposition technique to produce silver nanoparticles render the substrate bactericidal.

A variety of materials have been impregnated with silver to impart beneficially antimicrobial properties, with one example being wound dressings with antimicrobial properties. These dressings may range from simple gauze type dressings to animal derived protein type dressings such as collagen dressings; the composition of the particular dressing depends on the type of wound to be treated. Each of these dressings is used to particular type of wounds depending on their advantages, such as highly economical for simple abrasions and surgical incisions. The chronic wounds are best treated with polymer based dressings. Further polymer based wound dressings use various types of polymeric materials. Generally, they can be classified into two major classes, namely synthetic and naturally derived polymeric materials.

Synthetic materials include polyurethanes, polyvinylpyrolidone (PVP), polyethyleneoxide (PEO) and polyvinyl alcohol (PVA). These materials can be used in combination with other synthetic or natural polymers to achieve specific properties such as moisture retention, re-swelling capability, fluid (exudate) absorption capacity. Similarly, naturally derived polymers or biopolymers, such as collagen and alginates are also exploited for wound healing applications. They are used primarily due to their high water absorption/donating capacity. The biocompatible issue of a material comes to the fore when used for these anti-bacterial dressing applications. Even though they possess these excellent properties, they are usually expensive, and exhibit less exudates absorption and residue deposition on a wound site, thereby limiting their usage. Complimentary to these, hydrocolloid dressings also possess excellent properties that make it viable for wound dressing application. Compared to bacterial cellulose based wound dressing, however, they lack the moisture donating quality. Also, hydrocolloids are known to adhere to the wound bed, causing re-injury upon removal.

As an alternate material, bacterial synthesized cellulose possesses inherent characteristics allowing effective promotion of wound healing. Bacterial cellulose (BC) has certain advantages over plant cellulose, such as, better hydrophilic nature, three dimensional layered structures that allows effective moisture handling capability. Their native dimension and geometry in the fiber form of nanometers (<50 nm) results in high aspect ratio. This has an effect in the water absorption capability per unit area. Their high mechanical strength (78±17 GPa) makes it a unique biopolymer. Bacterial cellulose is highly hydrophilic with a water holding capacity ranging from 60 to 700 times its own weight as is described in U.S. Pat. No. 4,942,128. BC can handle high compressive stress. Ring et al. in U.S. Pat. Nos. 4,588,400, 4,655,758 and 4,788,168 discloses the superior properties of BC which can be modified to produce liquid loaded medical pads. In these studies, BC is produced in a static culture which were loaded with medicaments and liquids. Here, they explain the process of producing the cellulose in a static culture wherein the liquid levels were adjusted by undergoing a series of pressing and soaking to alter the liquid to cellulose ratio.

An artificial skin graft based on microbial cellulose has been disclosed by Farah et al. in their U.S. Pat. No. 4,912,049. This patent describes the method of producing microbial cellulose in a static culture using *Acetobacter xylinum*, and that is dehydrated while it is stretched. They also suggest the applicability of dehydrated microbial cellulose as an artificial skin substitute with no moisture donation capability and limited exudates absorption capacity.

Instead of producing BC in static cultures, Wan et al. in U.S. Pat. No. 5,846,213 disclosed the method of producing BC in stirred tank bioreactors. They were further dissolved in solvents which were then casted/molded into desired shape and size. The casted cellulose material possesses limited fluid absorption capacity. This also is devoid of the three dimensional structure that is present only in the pellicles produced by a static culture.

Although the above patents recognize the potential use of bacterial cellulose in medical applications, the prior literature has not produced a BC based antibacterial material that is capable of having a moisture management capability with inherent biocompatible nature of the cellulose. Also, an optimum wound healing material requires both liquid absorption/ releasing capabilities. The presence of growth factors and anti-microbial material enhances the rate of wound healing.

The present invention describes a procedure to incorporate nano-silver onto bacterial cellulose nanofibres. The antimicrobial properties are also demonstrated. The silver containing fibers can be shaped into any desired form. Alternatively, bacterial cellulose nanofibers can be pre-shaped before silver incorporation.

SUMMARY OF THE INVENTION

An antibacterial cellulose material comprised of silver nanoparticles bound to cellulose fibers is provided which exhibits antimicrobial properties. A method of producing these composite materials is also provided.

Thus there is provided a method of producing nano-silver coated cellulose fibers, comprising:

a) preparing a suspension of cellulose fibers at a pre-selected concentration;

b) exposing the cellulose fibers to an oxidizing agent for oxidizing the cellulose fibers to form dialdehyde cellulose fibers;

c) incorporating a functional group into a backbone of the dialdehyde cellulose fibers to produce functionalized cellulose fibers, the functional group being selected from the group consisting of thio-, aldehyde, ketone and carboxylic acid;

d) exposing the functionalized cellulose fibers to an aqueous solution containing a first silver compound such that nano-silver particles are formed and bound to the cellulose backbone of the functionalized cellulose fibers; and e) exposing the functionalized cellulose fibers with nano-silver particles bound thereto to a solution containing a second silver compound for growing the nano-silver particles to a pre-selected size.

In an embodiment, the cellulose may be bacterial cellulose produced using *Acetobacter xylinum* BPR 2001. The bacterial cellulose fibers are then oxidized with 0.16 M $NaIO_4$ solution for selected intervals of time to yield dialdehyde cellulose (DAC). These DAC nanofibres are then chemically treated to introduce the thio- (—SH) groups into the polymer matrix. They are then mixed with a silver proteinate (SP) solution to form bacterial cellulose fibres functionalized with silver nanoparticles of between about 15 nm to about 20 nm in diameter.

Accordingly, an embodiment of the present invention includes naturally derived cellulose and a method of synthesizing the same. The cellulose fiber of the present invention is a novel composite biomaterial which is not only biocompatible but also possesses antimicrobial properties. Additionally, the BC with antimicrobial activity can be used to make antibacterial clothes or clothing such as underwear, socks, shoe cushions, shoe linings, bed sheets, towels, hygiene products, laboratory coat, and patient clothes.

BRIEF DESCRIPTION OF THE DRAWINGS

The invention will be more fully understood from the following detailed description thereof taken in connection with the accompanying drawings, which form a part of this application, and in which:

FIG. 2A is the clear zone test of a film of bacterial cellulose sample used as control showing no bacterial inhibition (*E. coli*); FIG. 2B shows a clear zone of 3.5 mm (*E. coli*) for a film of bacterial cellulose loaded with silver using silver proteinate-sodium borate solution; and FIG. 2C illustrates the clear zone of 2.1 mm (*E. coli*) for a film of bacterial cellulose that has been functionalized with nanosilver using the silver nitrate-ammonia step.

FIG. 5 is an SEM micrograph showing the silver nanoparticles anchored to the microcrystalline cellulose substrate after the chemical treatment of being functionalized with silver and enhanced after 1 hour oxidation as described in Examples 1-4 and 6;

FIG. 6A is an SEM micrograph of a film of bacterial cellulose as is, without any treatment;

FIG. 6B represents the film of bacterial cellulose which is chemically treated as per Example 1-4, functionalized with silver nanoparticles after 1 hour of oxidation;

FIG. 7 is an Energy Dispersive X-ray (EDX) spectrum showing the positive identification of carbon, oxygen, sulphur and silver on a film of bacterial cellulose functionalized as described in Example 4 and Example 8;

FIG. 8A is the sample area where the EDX spectrum was obtained as shown in FIG. 7;

FIG. 8B is the sulphur map of the sample area shown in FIG. 8A;

FIG. 8C is the silver map of the sample area as shown in FIG. 8A; and

DETAILED DESCRIPTION OF THE INVENTION

Figure 1:
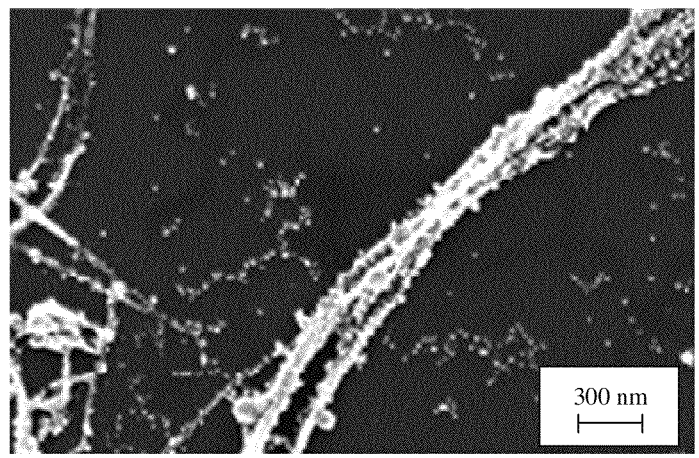
FIG. 1 is an SEM micrograph of bacterial cellulose enhanced with Silver (BC-Ag) after 1 hr oxidation as described in Example 4.

Generally speaking, the systems described herein are directed to an antimicrobial material comprising cellulose having silver nanoparticles incorporated into the cellulose fibers. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to an antimicrobial material comprising a cellulose having silver nanoparticles incorporated into the cellulose fibers.

As used herein, the term "about", when used in conjunction with ranges of dimensions of particles or other physical properties or characteristics, is meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present invention.

As used herein, the phrase "cellulose nanofibers" means fibres of cellulose having nanometer dimensions.

As used herein, the phrase "dialdehyde cellulose nanofibers" means those chemically modified 'cellulose nanofibers' with any oxidizing agent (such as, but not limited to $NaIO_4$) to introduce aldehyde groups in the cellulose polymer chain as per Example 2.

As used herein the phrase "silver proteinate" (SP) refers to the product resulting from the attachment of silver atoms to proteins and/or partially hydrolyzed proteins and is not restricted to any particular protein structure.

As used herein the phrase "free standing cellulose fibers" refers to the individual fibers including dialdehyde cellulose fibers prior to being formed into a sheet or any other shape.

The present invention provides a novel composite biomaterial that includes nanosilver particles in metallic form bound to bacterial cellulose. This antimicrobial bacterial cellulose of the present invention has a long-lasting antimicrobial effect and exhibits a broad-spectrum of antimicrobial activity. The bactericidal fibres are nanofibres of native dimension<50 nm, containing nanosilver particles having diameters in the two different ranges, namely, one of ~15 to about 50 nm and another of ~40 to about 100 nm. These nanosilver particles are chemically bound to the cellulose backbone, thus resulting in enhanced antimicrobial effects.

The fibers of the cellulose are preferably produced by a process involving fermentation of *Acetobacter xylinum* BPR 2001 in shaken and stirred tank reactors. The oxidation of the cellulose followed by silver incorporation can readily be scaled up for large scale production.

The antimicrobial cellulose of the present invention is non-toxic, safe, and thus, suitable for use in medical or healthcare related purposes, which can be used to make an antimicrobial cloth and wound dressing. The cloth is suitable for use as bandage, gauze, or surgery cloth. It can also be used in making clothes or clothing such as underwear, pantyhose, shoe cushions, shoe insole, shoe lining, bedding sheets, pillow sham, towel, hygiene products, medical robes etc. The capability of cellulose to be shaped into any required form gives the applicability an added technology advantage.

Thus the silver functionalized bacterial cellulose of the present invention showed lasting bactericidal activity against gram positive and gram negative bacteria; *S. aureus* and *E. coli* respectively. The antimicrobial effect of the present invention is derived from silver metals analogous to ionic silver. Although the exact inhibiting mechanism is still the subject matter of extensive research, it has an advantage over the use of conventional antibiotics since the use of silver as an antibacterial does not induce resistance in the microorganisms. These bacterial cellulose fibers could be dried or never dried even after the step of silver incorporation. The present invention is particularly suitable for use as cloth or clothes in disinfecting and treating patients with burn and scald-related skin infection, wound-related skin infection, skin or mucosa bacterial or fungal infection, surgery cut infection, vaginitis, and acne-related infection. Further they are applicable as anti-microbial wound dressings, individual fibres can be incorporated into medical device materials that require infection control. The BC-Ag/SP fibers can be molded into required shapes to suit a particular application, e.g. stents, wound dressings etc. They can be used to reinforce biomaterials to form nanocomposites that are antimicrobial.

The antimicrobial cellulose produced in accordance with the present invention is produced by reaction of silver with dialdehyde cellulose, in which the level of silver loading is a function of oxidation time.

Accordingly in a preferred embodiment the method of producing antimicrobial cellulose includes:
a) preparing a suspension of bacterial cellulose fibers at a pre-selected concentration,
b) carrying out the oxidation of the bacterial cellulose fibers at a particular concentration of the oxidizing agent,
c) adding thio- groups to the polymer backbone,
d) reacting the product in c) comprised of the polymer backbone with the incorporated thio- groups with silver proteinate-sodium borate solution to yield nano-silver particles bound to the cellulose backbone, and
e) adding silver nitrate-ammonia solution to enhance the nanosilver particle size.

The suspension produced in step a) above is a suspension of bacterial cellulose in distilled water. A concentration of 0.36 wt % bacterial cellulose was used. 5 mL of the 0.36 wt % bacterial cellulose was subjected to oxidation with an oxidant resulting in an oxidized dialdehyde cellulose. Examples of appropriate oxidants include, but are not limited to, gaseous chlorine, hydrogen peroxide, peracetic acid, chlorine dioxide, nitrogen dioxide (dinitrogen tetraoxide), persulfates, hypochlorous acid, hypohalites or periodates. Preferred oxidizing agents include alkaline metal periodates, with sodium or potassium periodate being most preferred.

The concentration of the oxidant in the solution depends on the extent of oxidation desired. In general, higher the concentration of oxidant or longer the reaction time, higher degree of oxidation is achieved. In an embodiment of the present invention, the oxidation reaction may be carried out using 0.16M $NaIO_4$ for a desired amount of time to achieve the desired level of oxidation. The oxidation reaction can be carried out at higher temperatures such as 70° C., depending on the type of oxidant used. The inventors have preferred using controlled oxidation at room temperature over a time range of 15-90 minutes.

In an embodiment of the invention, the suspension in b) was treated with 1% thiosemicarbazide (TSC) in 5% aqueous acetic acid at 60° C. for 90 minutes for the incorporation of —SH group. The significance of introducing the —SH group is to exploit the strong interaction between silver and the sulphur. The addition of thio- group to the cellulose in step c) can be can also be accomplished by using a variety of other —SH containing compounds, not just thiosemicarbazide.

The thio- containing compound may consist of $NH_2$—R—SH, where R is an alkyl group. Other possible functionalities that attract silver includes functional groups containing polar groups for example, oxygen, nitrogen, phosphorous and sulphur. Thus, while the use of sulphur in the examples disclosed herein is preferred because sulphur has the highest interaction with silver, but it will be appreciated that other functional groups can be used as well.

Silver proteinate solution was prepared by dissolving 1% wt silver proteinate (SP) and sodium borate (2% wt) in water which was filtered in a 0.45 μm filter and mixed with the thio-incorporated bacterial cellulose and kept in the dark for 1 hour. Instead of sodium borate, other water soluble borate salts could be used. It is noted that silver proteinate is a preferred material but other simple salts of silver could also be used. However silver proteinate is preferred in this step because silver attached to a protein moiety allows for better control of the silver particle size in a range from about 15 nm to about 20 nm.

The use of a silver salt (silver nitrate for example) in this first step would result in larger particle size and instead is preferred for use in the second step of exposure of the fibers having the nanosized silver particles for enhancing the already formed silver nanoparticle through silver proteinate reaction with the exposure to the silver salt solution being performed for a length of time selected to give silver nanoparticles having said pre-selected size in a range from about 50 nm to about 100 nm.

A further embodiment of this invention includes treating 1 mL of sample from step d) with silver-ammonia solution (5 mL) in a vial cleaned with nitric acid and maintaining it at 95° C. for 3-6 minutes to produce silver nanoparticles of enhanced size (50 to 100 nm). The hot mixture is then washed with deionised water. Silver-ammonia solution is prepared by dissolving 1 g of silver nitrate in 8 mL of water and adding ammonium hydroxide drop-wise until dissolution of the brown precipitate that forms. This solution is diluted to 75 mL and filtered through a 0.45 μm membrane filter and stored in the dark. In addition to silver nitrate other water soluble silver compounds are also usable. A variety of other silver salts that can be dissolved to form an aqueous solution may be used as well. A preferred silver containing solution is silver nitrate since it is one of the most common water soluble silver compounds. Other silver salts that could be used include, but are not limited to, silver sulfate, silver acetate, silver bromide etc.

Figure 3:
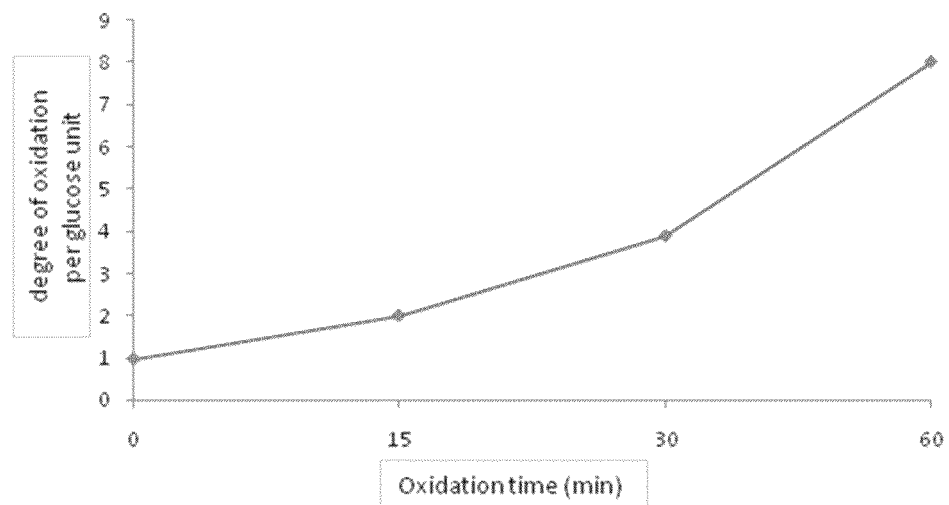
FIG. 3 indicates the degree of oxidation of bacterial cellulose films at particular intervals of time of oxidation as described in Example 7.

The amount of silver incorporated is proportional to the aldehyde sites available for thio- groups to bind. In other words the amount of aldehyde moieties is proportional to the amount of thio- groups, which is proportional to the amount of silver on the polymer backbone. FIG. 3 shows the percentage of aldehyde groups per glucose unit of cellulose, where glucose is the monomer of cellulose.

It is noted that the silver in metallic form is incorporated into the cellulose in step d) above. The resulting antimicrobial cellulose material has the advantages of long-lasting antimicrobial effect, broad spectrum antimicrobial activity, non-toxic, non-stimulating, natural, and suitable for medicinal uses. The antimicrobial activity of the material is stronger when in contact with liquid, due to the anchored silver nanoparticles. The commercially available silver wound dressings are of ionic silver based and metallic nano-silver, in which the metallic silver is formed by a physical vapour deposition technique.

Dressings produced by physical vapour deposition have far more silver than is necessary for treating wounds, which when used on a long term basis results in the formation of skin scars. Moreover, permanent staining (black) of tissue by free silver at the healed wound site is highly undesirable from the aesthetic point of view. The material thus produced by undergoing d) and e) is found to exhibit antimicrobial properties against both gram positive and gram negative bacteria including but not limited to *Eschericia coli* and *Staphylococcous aureus*.

Figure 2A:
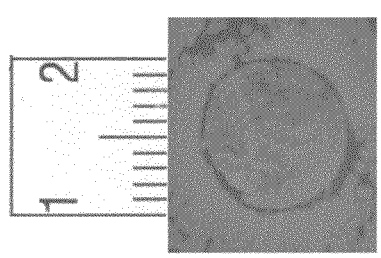
FIGS. 2A-2C show a clear zone test done on *E. coli* after 3 days using BC-SP (SP refers to "silver proteinate") and BC-Ag samples that were oxidized for 1 hr as described in Example 5; where
Figure 2B:
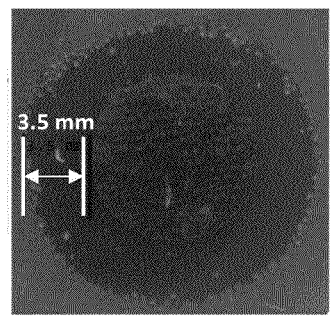
Figure 2C:
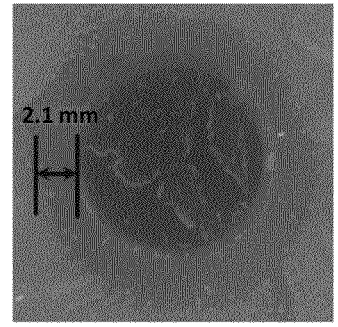
Figure 9:
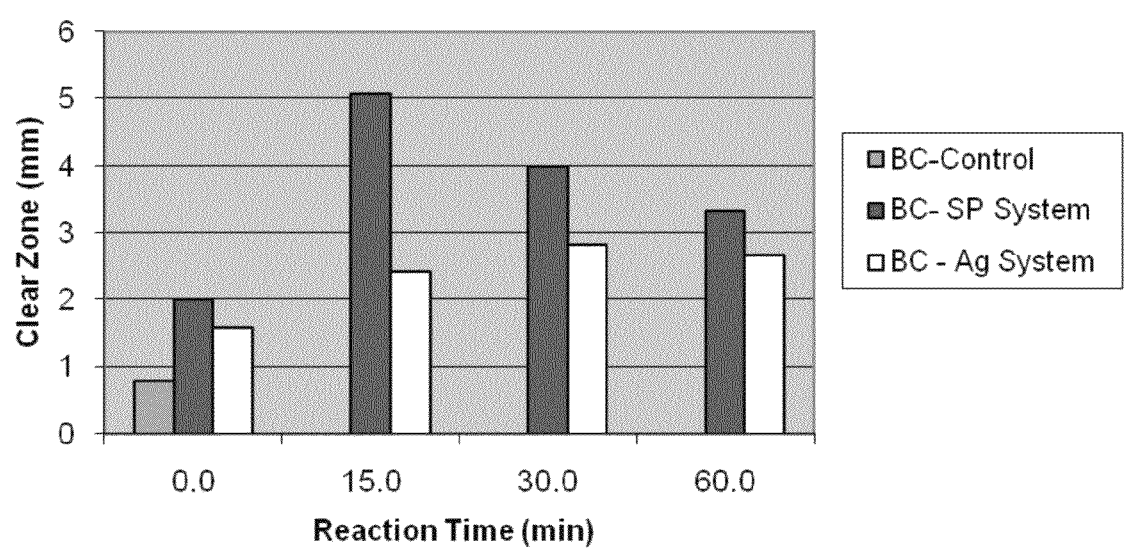
FIG. 9 illustrates the results of clear zone tests showing the relative clear zone radius of bacterial cellulose functionalized with silver nanoparticles as per BC-SP and BC-Ag systems. These samples were prepared as describe in Examples 1-4.

The amount of silver does not necessarily result in higher bactericidal activity. In another embodiment of the invention we demonstrate the higher bactericidal activity of BC-SP system as compared to BC-Ag system using *E. coli* as the model bacteria. FIGS. 2B and 2C represent the higher zone of inhibition of *E. coli* in BC-SP system by 65% as compared to BC-Ag system. We corroborate with Taylor et al (2005), *Biomaterials*, Vol. 26, p. 7230-7240 that the size dependence of silver nanoparticles with the bactericidal activity. Taylor et. al. reported the improved antibacterial activity when silver nanoparticles lesser than 32 nm which correspond to our BC-SP system. FIG. 9 shows that BC-SP always exhibits higher antibacterial activity than BC-Ag possibly due to the size of silver nanoparticles and 15 minutes oxidized BC-SP system shows highest activity against *E. coli*.

In another embodiment of the invention, the silver nanoparticles are chemically attached to the polymer (cellulose) matrix. This greatly reduces the possibility of the silver nanoparticles leaching out of the polymer/substrate matrix when in contact with the wound site/water. Poon et al. *Burns* (2004) Vol. 30, p. 140-147, demonstrate the cytotoxicity of the Acticoat™ on kerarinocytes and fibroblasts, which are primarily due to unbound silver nanoparticles from the matrix to the wound site. The present invention chemically binds the silver nanoparticles to the polymer backbone, which is clearly observed from FIG. 1 and FIG. 5. Energy Dispersive X-ray spectrum (EDX) positively identifies the particles as silver in FIG. 7. A mapping of sulphur and silver groups indicate that silver nanoparticles are bound to the substrate through the thio- groups, as shown in FIG. 8. Quantitative measurement of Sulphur to Silver ratio can also be obtained from Table 1. Thus our bacterial cellulose based antibacterial material shows improved bacterial activity over longer periods of usage.

In the dressings disclosed herein, it is possible to vary the size of the nanosilver particles in a range from about 10 nm to about 100 nm. Bacterial cellulose is known for its excellent water absorbing capacity, thus maintaining the optimum humidity for wound healing. This coupled with antibacterial agent i.e., metallic silver enhances bacterial inhibition. In addition, BC being a natural nanomaterial with which we have demonstrated the antimicrobial activity is much more reliable compared to synthetic material for its biocompatibility and other biomedical parameters that come along.

The inventors have also found that BC-SP system inhibits bacteria much better than those of BC-Ag system. Compared to disclosure by Burrell et al. using physical vapour deposition, this is chemically bound to the substrate material with sustained release of silver over a longer period of time. Also, the concentration of the silver can be increased in any particular dressing per unit area by enhancement as in step (e).

While the method described above is a preferred method, it will be understood that variations are possible, for example instead of functionalizing the polymer backbone with thio- groups, it may instead be functionalized with several alternatives including aldehyde, ketone, carboxylic acid groups and any other chemical functionalities that exhibit positive chemical interaction with silver.

While a preferred cellulose disclosed herein is bacterial cellulose, it will be appreciated by those skilled in the art that other types of cellulose may be used. For example microcrystalline cellulose which has been functionalized with nanosilver as in Example 6. Many other polysaccharides, with a monomer unit of the form shown below, where n is the number of repeating monomer unit, can also be employed to functionalize with nano metallic silver. The polysaccharide can be dextran, amylose etc., and its derivatives.

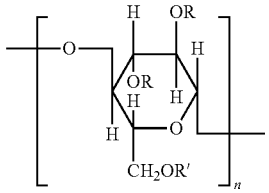

where R and R' = H or alkyl group,
n is the number of repeating units

The present invention is further illustrated by the following non-limiting examples.

EXAMPLE 1

Bacterial Cellulose Production

Bacterial cellulose was produced by fermentation using *Acetobacter xylinum* BPR 2001 in a media containing fructose (2% wt) and corn steep liquor (8% v) were used as the carbon and nitrogen source respectively as per Joseph et al. (2003) *Journal of Chemical Technology and Biotechnology*, Vol. 78, p. 964-970 and Guhados et al (2005) *Langmuir*, Vol. 21, p. 6642-6646. The bacterial cellulose fibers were then subjected to 1% wt NaOH treatment for 30 min at 90° C. to lyse the bacteria and centrifuged to get pure cellulose, which is stored at 4° C.

EXAMPLE 2

Preparation of Dialdehyde Cellulose from Bacterial Cellulose
i) Freestanding Bacterial Cellulose Fibres Modified with Aldehyde Moieties:
5 mL of 0.36 wt % bacterial cellulose were oxidized with 0.16 M $NaIO_4$ for 15 minutes, 30 minutes and 1 hour respectively. Zero (0) time oxidation refers to the control without any oxidation while the scheme of reaction remains unchanged.
ii) Films of Bacterial Cellulose Containing Aldehyde Moieties:
In the case of preparing films of dialdehyde cellulose (DAC), the resulting bacterial cellulose fibres from Example 1 were cast to form a non-woven sheet of bacterial cellulose with dry weight of 0.05 g, after which the films were oxidized using 25 mL of 0.16M $NaIO_4$ at room temperature in the dark.
In both above cases, the oxidized product is dialdehyde cellulose (DAC) in fibre or film form which was recovered by washing in ethylene glycol and then washed with distilled water.

EXAMPLE 3

Thio- Incorporation onto the Bacterial Cellulose Matrix
The DAC thus obtained was mixed with 1% thiosemicarbazide (TSC) in 5% aqueous acetic acid. The mixture was kept at 60° C. for 90 minutes, after which the sample was washed and collected by centrifugation.

Films of dialdehde cellulose from Example 2 was reacted with thiosemicarbazide through Example 3 to incorporate thio- groups to the cellulose backbone.

EXAMPLE 4

Silver Decoration of Bacterial Cellulose:
The sample of thio- modified bacterial cellulose fibres was suspended in water (1 mL) and mixed with a freshly prepared solution of 1% silver proteinate (SP) in 2% sodium borate (5 mL), which was filtered through a 0.45 µm cellulose nitrate filter. The mixture was kept in darkness for 1 hr at room temperature and diluted with water for centrifugation. This produces BC functionalized with silver of size of the order of ~15 nm.
This TSC-SP treated sample (1 mL) was mixed with silver-ammonia solution (5 mL) in a vial cleaned with nitric acid and was maintained at 95° C. for 3-6 minutes to produce silver nanoparticles coated bacterial cellulose (BC-Ag) of enhanced size (50 to 100 nm). The hot mixture was then washed with deionised water. FIG. 1 is a SEM micrograph of the bacterial cellulose enhanced with Silver (BC-Ag) after 1 hr oxidation. FIG. 6B is a SEM micrograph of a film of bacterial cellulose enhanced with silver (BC-Ag) after 1 hour of oxidation. The morphological difference of the nanofibre could be observed without silver nanoparticles in FIG. 6A where the SEM is that of a film of bacterial cellulose without any chemical treatment.
It could also be noted that silver functionalization by Examples 2-4 can be done on preformed sheets (both dry and never dry) of bacterial cellulose and/or free standing fibres (both dry/nondry) of bacterial cellulose.
The silver-ammonia solution was prepared by dissolving 1 g of silver nitrate in 8 mL of water and adding ammonium hydroxide drop-wise until dissolution of the brown precipitate that forms. This solution was diluted to 75 mL and filtered through a 0.45 µm membrane filter and stored in the dark. This stock solution was freshly filtered every time before use.

EXAMPLE 5

Antimicrobial Activity of Silver Decorated Bacterial Cellulose:
Nonwoven films of bacterial cellulose with different conditions namely, no oxidation (control) and with oxidation at 0 min, 15 min, 30 min and 1 hr followed by silver proteinate reaction using d) and silver enhancement reaction by e) were prepared. The antimicrobial activity of BC-SP and BC-Ag were tested against gram-positive *Saphylococcus aureus* and gram-negative *Escherichia coli* DH5α. The agar plates containing the control and the test samples were incubated at 37° C. for 3 days.
The clear zone demonstrates excellent bactericidal activity against the above said bacteria and shows evidence of nanosilver size dependence in the bacterial inhibition. FIGS. 2A-2C show a clear zone test done on *E. coli* after 3 days using BC-SP and BC-Ag samples that were oxidized for 1 hr showing representative clear zones. No colony or sign of any microbial growth was observed on the agar plate of the silver-loaded films, as opposed to those of the control group where signs of microbial growth were seen. Sample of bacterial cellulose film coated with silver nanoparticles belonging to BC-SP system as shown in FIG. 2B exhibits higher antibacterial activity as compared bacterial cellulose coated with nanosilver of BC-Ag system shown in FIG. 2C, while a film of bacterial cellulose as shown in FIG. 2A demonstrated no antibacterial activity. Quantitative measurement of the clear zone radius indicates the innate relationship between bactericidal activity and silver particle size. FIG. 9 indicate that bacterial cellulose coated with silver nanoparticles belonging to BC-SP system exhibit higher antimicrobial activity compared to BC-Ag system. And highest antibacterial activity was demonstrated by cellulose oxidized for 15 minutes and functionalized with silver nanoparticles belonging to the class of BC-SP.

EXAMPLE 6

Figure 4:
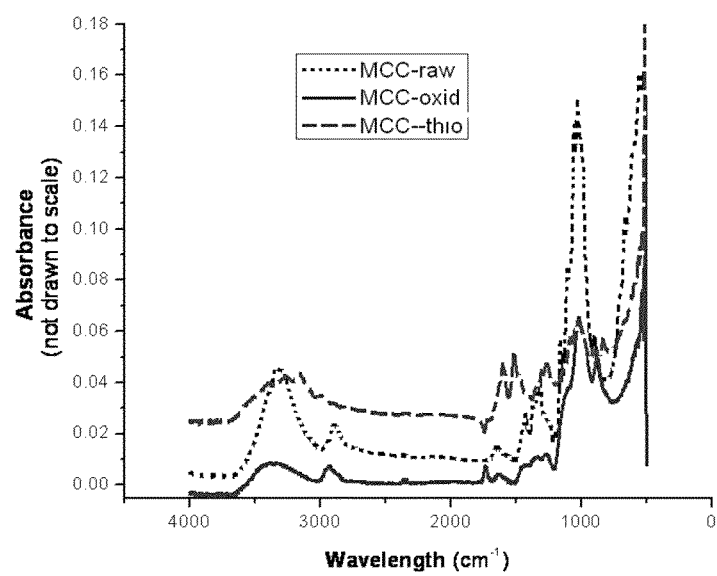
FIG. 4 shows FTIR Spectra of Microcrystalline cellulose (in dotted lines), after oxidation (solid line) and after thio-treatment (in hatched lines) as described in Example 6.

Spectroscopic Analysis of Microcrystalline Cellulose:

Microcrystalline cellulose (MCC) were treated with the above said three step silver functionalization and further enhanced with silver nitrate-ammonia solution. FIG. 4 shows the FTIR fingerprint of chemically modified microcrystalline. Oxidized MCC shows characteristic bands at 1735 cm$^{-1}$ and 880 cm$^{-1}$, corresponding to carbonyl and hemiacetal group stretching respectively. After thiosemicarbazide treatment sharp peaks at 1602 cm$^{-1}$ corresponding to C=N stretch appears while the peak of oxidized cellulose disappears. This indicates the reaction between aldehyde cellulose and the thiosemicarbazide. Further —NH groups present in the thiosemicarbazide are observed at 1515 cm$^{-1}$. FIG. 5 illustrates the fact the silver is bound to the cellulose substrate is observed.

EXAMPLE 7

Degree of Oxidation

The degree of oxidation is related to the amount of silver loaded on the cellulose substrate. Films of cellulose and oxidized cellulose were treated with 10 mL of 0.05M NaOH at 70° C. for 25 minutes. Following which 10 mL 0.05 M of HCl is added to neutralize the NaOH. At this stage, both molarities have to be equal. Following this, the solution with cellulose were then titrated against 0.01 M NaOH with phenolphthalein as the indicator. Let $V_1$ L be the volume of NaOH consumed per glucose unit of cellulose. Let $V_b$ be the volume of blank titrated with 0.01 M NaOH without cellulose. The molarities chosen are for desired accuracy and are not limited to the above values.

Percentage of oxidation=[(($V_1-V_b$)*Normality of NaOH)/(dry wt. of cellulose film/Molar mass of glucose unit)]*100

Thus the degree of oxidation is given as:

Percentage of oxidation=[(($V_1-V_b$)*0.01)/(0.05/162.145)]*100

FIG. 3 details the percentage of aldehyde groups per glucose unit of cellulose.

EXAMPLE 8

Energy Dispersive X-Ray (EDX) Spectroscopic Study of Silver Decorated Bacterial Cellulose Films of bacterial cellulose functionalized with nanosilver were subjected to EDX analysis which confirms the positive presence of silver as indicated by the EDX spectrum in FIG. 7. Table 1 indicated the amount of silver in weight percent present in the sample area as shown in FIG. 8A. To confirm the chemical interaction of silver to the polymer (cellulose) backbone is through the sulphur moieties, an EDX mapping of sulphur and silver was done. FIG. 8B indicates the presence of sulphur (as white dots) in the sample area shown in FIG. 8A, which corresponds to the presence of silver (as white dots) in the sample area shown in FIG. 8C. This confirms that silver is attached to the polymer through sulphur groups in thio-moiety.

Very advantageously, the silver containing bacterial cellulose (BC) fibers possess antimicrobial properties inhibiting a wide range of bacteria. Also, they can exhibit the bactericidal properties over a long period of time. The cellulose nanofibres can be in its native colour or dyed due to silver reaction.

As used herein, the terms "comprises", "comprising", "including" and "includes" are to be construed as being inclusive and open-ended. Specifically, when used in this document, the terms "comprises", "comprising", "including", "includes" and variations thereof, mean the specified features, steps or components are included in the described invention. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

TABLE 1

Quantitative Measurement of Carbon, Hydrogen, Sulphur and Silver in a film of bacterial cellulose

| Element | Weight % |
| --- | --- |
| C | 29.48 |
| O | 42.46 |
| S | 2.10 |
| Ag | 25.95 |
| Total | 100.00 |

What is claimed is:

1. A nanocomposite material comprising:
cellulose fibers functionalized with a functional group, the functional group having silver proteinate bound thereto; and
silver nanoparticles bound to the cellulose fibers, the silver nanoparticles comprising the silver proteinate.

2. The nanocomposite material according to claim 1 wherein said cellulose fibers are nanocellulose fibers.

3. The nanocomposite material according to claim 2 wherein said silver nanoparticles have a diameter between approximately 10 nm and 100 nm.

4. The nanocomposite material according to claim 2 wherein said nanocellulose fibers are bacterial cellulose nanofibers.

5. The nanocomposite material according to claim 4 wherein said nanocellulose fibers are produced by the bacteria Acetobacter xylinum (Gluconacetobacter xylinus).

6. The nanocomposite material according to claim 2 wherein said silver nanoparticles are bound to said nanocellulose fibers through thio-groups.

7. The nanocomposite material according to claim 2 wherein said silver nanoparticles are bound to said nanocellulose fibers through a functional group selected from the group consisting of aldehyde, ketone, and carboxylic acid.

8. The nanocomposite material according to claim 2 wherein a weight percent of said silver nanoparticles is approximately 25%.

9. The nanocomposite material according to claim 2 wherein said silver nanoparticles have a diameter between approximately 15 nm and 50 nm.

10. The nanocomposite material according to claim 2 wherein said silver nanoparticles have a diameter between approximately 15 nm and 20 nm.

11. The nanocomposite material according to claim 2 wherein said silver nanoparticles have a diameter between approximately 40 nm and 100 nm.

12. The nanocomposite material according to claim 2 wherein said silver nanoparticles have a diameter between approximately 50 nm and 100 nm.

13. The nanocomposite material according to claim 1 wherein said cellulose fibers are microcrystalline cellulose fibers.

14. The nanocomposite material according to claim 1 having a bactericidal activity that is effective against gram positive and gram negative bacteria.

15. The nanocomposite material according to claim 1 having a bactericidal activity that is effective against *S. aureus* and *E. coli*.

16. The nanocomposite material according to claim 1 wherein said cellulose fibers are free standing.

17. The nanocomposite material according to claim 1 wherein said cellulose fibers form a non-woven sheet.

18. A wound dressing comprising a nanocomposite material according to claim 1.

19. An antimicrobial cloth comprising a nanocomposite material according to claim 1.

20. A medical device comprising a nanocomposite material according to claim 1.

21. An article of clothing comprising a nanocomposite material according to claim 1.

22. A nanocomposite material comprising a polysaccharide coated with silver nanoparticles, wherein said polysaccharide comprises a monomer unit of the form:

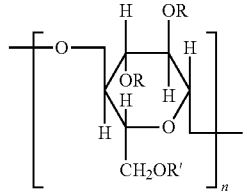

where R and R' are H or an alkyl group;
wherein silver proteinate is bound to the polysaccharide, and
wherein the silver nanoparticles comprise silver proteinate.

23. The nanocomposite material according to claim 22 wherein said polysaccharide is selected from the group consisting of dextran, amylose, and derivatives thereof.

* * * * *